United States Patent [19]

Miyazawa et al.

[11] Patent Number: 5,468,419

[45] Date of Patent: * Nov. 21, 1995

[54] PREPARATION OF $C_9$ ALCOHOL MIXTURE AND PLASTICIZER

[75] Inventors: Chihiro Miyazawa; Souichi Orita; Akio Tsuboi, all of Kurashiki, Japan

[73] Assignee: Mitsubishi Chemical Corporation, Tokyo, Japan

[ * ] Notice: The portion of the term of this patent subsequent to Feb. 23, 2010, has been disclaimed.

[21] Appl. No.: 740,403

[22] Filed: Aug. 5, 1991

Related U.S. Application Data

[63] Continuation of Ser. No. 738,916, Aug. 1, 1991, Pat. No. 5,189,105, which is a continuation of Ser. No. 438,569, Nov. 20, 1989, abandoned, which is a continuation of Ser. No. 152,495, Feb. 5, 1988, abandoned.

[30] Foreign Application Priority Data

Feb. 9, 1987 [JP] Japan .................................. 62-27561

[51] Int. Cl.$^6$ .............................. C09K 3/00; C07C 27/20
[52] U.S. Cl. ................... 252/182.12; 106/311; 252/364; 560/76; 568/454; 568/909
[58] Field of Search ........................... 252/182.12, 364; 106/311; 560/76; 568/454, 909

[56] References Cited

U.S. PATENT DOCUMENTS

| | | | |
|---|---|---|---|
| 2,880,241 | 3/1959 | Hughes | 568/909 |
| 4,053,438 | 10/1977 | DeSimone | 252/522 |
| 4,291,127 | 9/1981 | Akabayashi et al. | 560/76 |
| 4,312,779 | 1/1982 | Quick | 568/909 |
| 4,376,212 | 3/1983 | Ohyama et al. | 526/328 |
| 4,426,542 | 1/1984 | Barker et al. | 568/909 |
| 4,443,638 | 4/1984 | Yates | 568/454 |
| 4,463,211 | 7/1984 | Manning | 585/515 |
| 4,711,968 | 12/1987 | Oswald et al. | 568/454 |
| 4,776,947 | 10/1988 | Streck et al. | 208/262.1 |
| 4,822,917 | 4/1989 | Miyazawa et al. | 568/454 |
| 4,969,953 | 11/1990 | Miyazawa et al. | 106/311 |
| 5,072,057 | 10/1991 | Oswald et al. | 568/454 |
| 5,189,105 | 2/1993 | Miyazawa et al. | 252/182.12 |

FOREIGN PATENT DOCUMENTS

| | | |
|---|---|---|
| 636218 | 2/1962 | Canada . |
| 52999 | 2/1982 | European Pat. Off. . |
| 183547 | 6/1986 | European Pat. Off. . |
| 1027194 | 4/1958 | Germany . |
| 54-88206 | 9/1979 | Japan . |
| 789777 | 1/1958 | United Kingdom . |

OTHER PUBLICATIONS

Patent Abstracts of Japan, unexamined applications, C section vol. 3, No. 109, Sep. 12, 1979 The Patent Office Japanese Government p. 81 C 58.
Chemical Systems, Inc., "Process Evaluation and Research Planning", 3rd Quarterly Report, Jun. 1981, pp. 325–344.
PCV Technology, Fourth Edition, W. V. Titow, 1984, pp. 136–138 and 153–156.

Primary Examiner—Edward A. Miller
Attorney, Agent, or Firm—Oblon, Spivak, McClelland, Maier & Neustadt

[57] ABSTRACT

A $C_9$ alcohol mixture for plasticizer obtained by the hydroformylation and hydrogenation of a $C_8$ olefin mixture as the starting material obtained by the dimerization of a butene fraction, said alcohol mixture comprising from 8 to 50% by weight of a first group component having a retention time not longer than the retention time of isobutyl n-caprylate, from 8 to 40% by weight of a second group component having a retention time longer than that of isobutyl n-caprylate and not longer than that of methyl n-caprate and from 20 to 80% by weight of a third group component having a retention time longer than that of methyl n-caprate, as divided into such three components by gas chromatography using a capillary column packed with a polyethylene glycol having a number average molecular weight of 15,000 to 20,000 as an isomer separating agent.

14 Claims, No Drawings

# PREPARATION OF C$_9$ ALCOHOL MIXTURE AND PLASTICIZER

RELATED APPLICATIONS

This application is a continuation of U.S. application Ser. No. 07/738,916 filed Aug. 1, 1991, now U.S. Pat. No. 5,189,105, which is a continuation of U.S. application Ser. No. 07/438,569 filed Nov. 20, 1989, abandoned, which is a continuation of U.S. application Ser. No. 07/152,495 filed Feb. 5, 1988, abandoned.

The present invention relates to an alcohol mixture for plasticizer. More particularly, the present invention relates to a C$_9$ alcohol mixture having excellent heat resistance, cold resistance and electrical insulating properties as an alcohol material for plasticizer for a vinyl chloride resin.

It is known that a C$_9$ alcohol mixture obtained by the hydroformylation and hydrogenation of a C$_8$ olefin mixture (hereinafter referred to as "octenes") as the starting material obtainable by the dimerization of a C$_4$ fraction (hereinafter referred to as a "butene fraction") composed mainly of butene which is obtainable in a large quantity by the thermal decomposition of naphtha or by the catalytic decomposition of heavy or light oil, can be suitably employed as a starting material for plasticizer for a vinyl chloride resin. It is also known that the C$_9$ alcohol mixture has excellent heat resistance and is useful as an alcohol material for plasticizer, as disclosed in UK Patent No. 789,777.

However, such a C$_9$ alcohol mixture is a mixture of many kinds of isomers since octenes obtainable primarily by the dimerization of the butene fraction include many isomers, and the properties of the plasticizer vary substantially depending upon the composition of these isomers, whereby a substantial difference will be brought about in the cold resistance, the electrical insulating properties, etc. as the important properties of a vinyl chloride resin.

Accordingly, improvement of the properties of the C$_9$ alcohol mixture is one of the most important subjects to those skilled in the art. However, because of the comprexity, not very much has been known for the improvement of the properties. Especially, little has been known for a method of obtaining a C$_9$ alcohol mixture for plasticizer which is excellent in both the cold resistance and the electrical insulating properties.

In view of the above-mentioned conventional techniques, the present inventors have conducted extensive reseach to obtain an alcohol mixture for plasticizer which is excellent in both the cold resistance and the electrical insulating properties and as a result, have found that a C$_9$ alcohol mixture obtained by hydroformylating octenes obtainable by the dimerization of a butene fraction, followed by hydrogenation, which has a specific distribution of the isomers such that when the isomers are divided into certain specific three group components, the proportions of the respective group components are within certain specific ranges, exhibits excellent performance in both the cold resistance and the electrical insulating properties when used for plasticizer. The present invention has been accomplished on the basis of this discovery.

Namely, the object of the present invention is to provide a C$_9$ alcohol mixture exhibiting excellent performance in the cold resistance, the heat resistance and the electrical insulating properties as the alcohol material for plasticizer for a vinyl chloride resin.

In the broadest sense, the present invention provides a C$_9$ alcohol mixture for plasticizer obtained by the hydroformylation and hydrogenation of a C$_8$ olefin mixture as the starting material obtained by the dimerization of a butene fraction, said alcohol mixture comprising from 8 to 50% by weight of a first group component having a retention time not longer than the retention time of isobutyl n-caprylate (i.e. octanoic acid isobutyl ester), from 8 to 40% by weight of a second group component having a retention time longer than that of isobutyl n-caprylate and not longer than that of methyl n-caprate (i.e. decanoic acid methyl ester) and from 20 to 80% by weight of a third group component having a retention time longer than that of methyl n-caprate, as divided into such three components by gas chromatography using a capillary column packed with a polyethylene glycol having a number average molecular weight of 15,000 to 20,000 as an isomer separating agent.

Now, the present invention will be described in detail with reference to the preferred embodiments.

The butene fraction as the starting material for the alcohol mixture for plasticizer of the present invention may be a C$_4$ fraction (hereinafter referred to as a "BB fraction") obtained by the thermal decomposition of naphtha or a BB fraction obtained by the catalytic decomposition of heavy or light oil.

The BB fraction obtained by the thermal decomposition of naphtha may directly be dimerized. However, a so-called spent BB fraction obtained by separating butadiene out of the BB fraction by extraction, or a so-called spent spent BB fraction obtained by further separating isobutene out of the spent BB fraction, may also be suitably employed.

The BB fraction obtained by the catalytic decomposition of heavy or light oil is a mixture composed mainly of butene and butane. This fraction may be directly dimerized for use. However, a BB fraction obtained by separating isobutene out of such a fraction by e.g. distillation may also be suitably used.

Such a butene fraction can be dimerized by a usual dimerization reaction. For example, the dimerization may be conducted by a so-called Ziegler catalyst method wherein a nickel salt and an aluminum-alkyl halide are used as the catalyst, or by an acid catalyst method wherein solid phosphoric acid is used as the catalyst.

The C$_8$ olefin mixture obtained by the dimerization of the BB fraction comprises various isomers, all of which are useful as the starting material for the hydroformylation reaction.

The hydroformylation reaction can be conducted by a conventional method. As the catalyst, any catalysts commonly employed for the hydroformylation reaction on an industrial scale, such as a rhodium catalyst or a cobalt catalyst, may be employed.

The hydroformylation reaction using rhodium as the catalyst is usually conducted under reaction condition such that the rhodium concentration is from 0.1 to 100 ppm as rhodium atom, the temperature is from 80° to 200° C., the pressure is from atmospheric pressure to 500 kg/cm$^2$G and the H$_2$/CO volume ratio is from 0.5 to 4. Further, the rhodium catalyst may be employed as modified by a ligand such as a triarylphosphine (e.g. triphenylphosphine). No solvent is usually required. However, it is possible to use an organic solvent inert to the reaction.

The hydroformylation reaction using cobalt as the catalyst, is usually conducted under a reaction condition such that the cobalt concentration is from 0.05 to 10% by weight as cobalt atom, the temperature is from 80° to 180° C., the pressure is from 50 to 300 kg/cm$^2$G and the H$_2$/CO volume ratio is from 0.5 to 4. Further, the cobalt catalyst may be used as modified by a ligand such as a triarylphosphine (e.g. triphenylphosphine). No solvent is usually required. However, it is possible to employ an organic solvent inert to the reaction.

The C$_9$ aldehyde mixture or a mixture of C$_9$ aldehydes and $C_9$ alcohols obtained by the above hydroformylation reaction of the $C_8$ olefin mixture, is usually converted to $C_9$ alcohol mixture by a hydrogenation reaction. The hydrogenation reaction is usually conducted under a pressure of at least atmospheric pressure, preferably from 30 to 300 atm, at a temperature of at least room temperature, preferably from 100° to 200° C., by using a usual hydrogenation catalyst such as nickel, chromium or copper.

The crude alcohol mixture thus obtained is then purified by distillation in a rectification tower. The rectification of the crude alcohol mixture is usually conducted by using a distillation tower having a theoretical number of plates of from 3 to 50 plates under a condition such that the tower top pressure is from a few mmHg to 760 mmHg and the tower top temperature is from 50° to 220° C.

The alcohol mixture for plasticizer of the present invention may readily be obtained by a method wherein the amount of the distillate during the rectification is controlled to obtain the composition within the range of the present invention, or by a method wherein the distillate is finely classified and the classified fractions are suitably mixed to obtain the composition of the present invention.

The composition of the alcohol mixture for plasticizer thus obtained will be determined as follows. Firstly, by using a polyethylene glycol having a number average molecular weight of from 15,000 to 20,000 as an isomer separating agent (packing agent), the alcohol mixture obtained as above is analyzed by gas chromatography using a capillary column packed with the packing agent, and the detected isomer components are divided into three group components based on the retention times of two internal standard substances isobutyl n-caprylate and methyl n-caprate). Namely the first internal standard substance is isobutyl n-caprylate, and the second internal standard substance is methyl n-caprate.

The analytical condition by the gas chromatography using a capillary column packed with the above-mentioned packing agent, is for example as follows.

(1) Column: Packing agent "polyethylene glycol 20M" (manufactured by Gasukuro Kogyo Inc.), FFS (flexible fused silika) capillary column having a wall thickness of 0.15 μm, a length of 50 m and a diameter of 0.25 mm.

(2) Detector: FID (hydrogen flame ionization detector).

(3) Carrier gas: Helium gas, capillary: 0.66 ml/min, purge: 43.56 ml/min.

(4) Combustion gas: Hydrogen: 0.6 kg/cm²G Air: 0.8 kg/cm²G (5) Temperature conditions:
Initial temperature of the column: 80° C. temperature rise after 8 minutes: 4.5° C./min, final temperature: 180° C. The temperature at the inlet and in the detector: 230° C.

(6) Time for analysis: 40 minutes.

(7) Quantitative method: Internal standard method using n-undecane as the internal standard substance (IS).

$C_9$ alcohol mixture (sample)/IS=10/1 (weight ratio), amount of sample=0.2 μl, relative mol sensitivity of alcohol=1.0.

The $C_9$ alcohol mixture obtained as above is thus analyzed, whereupon isomers having a retention time not longer than the retention time of isobutyl n-caprylate are grouped into a first group component, isomers having a retention time longer than the retention time of isobutyl n-caprylate and not longer than the retention time of methyl n-caprate are grouped into a second group component and isomers having a retention time longer than the retention time of methyl n-caprate are grouped into a third group component.

In the present invention, the $C_9$ alcohol mixture is required to have a composition comprising from 8 to 50% by weight of the first group component, from 8 to 40% by weight of the second group component and from 20 to 80% by weight of the third group component. A preferred composition comprises from 10 to 50% by weight of the first group component, from 10 to 40% by weight of the second group component and from 30 to 70% by weight of the third group component. A more preferred composition comprises from 10 to 35% by weight of the first group component, from 10 to 40% by weight of the second group component and from 30 to 70% by weight of the third group component. A further preferred component comprises from 15 to 35% by weight of the first group component, from 10 to 40% by weight of the second group component and from 30 to 65% by weight of the third group component. A still further preferred composition comprises from 20 to 35% by weight of the first group component, from 10 to 40% by weight of the second group component and from 30 to 60% by weight of the third group component. The most preferred composition comprises from 20 to 30% by weight of the first group component, from 15 to 33% by weight of the second group component and from 35 to 60% by weight of the third group component. If the first group component is less than 8% by weight, the electric insulating properties tend to deteriorate. On the other hand, if it exceeds 50% by weight, the heat resistance and the cold resistance tend to deteriorate. Further, if the third group component is less than 20% by weight, the heat resistance and the cold resistance tend to deteriorate, and if it exceeds 80% by weight, the electrical insulating properties tend to deteriorate.

The $C_9$ alcohol mixture of the present invention thus obtained may be reacted with e.g. phthalic anhydride by a usual method for esterification and then purified by a usual method to obtain a plasticizer (such as a phthalate plasticizer).

When a vinyl chloride polymer and the above plasticizer are mixed in predetermined proportions and the properties of the plasticizer are compared with e.g. a conventional his (2-ethylhexyl) phthalate prepared from 2-ethylhexanol, the plasticizer obtained by the present invention is excellent in both the cold resistance and the electrical insulating properties and has superior properties as a whole, although it may be inferior to some extent in the plasticizing efficiency.

Now, the present invention will be described in detail with reference to Examples. However, it should be understood that the present invention is by no means restricted to such specific Examples.

EXAMPLE 1

(1) Preparation of octenes

A $C_4$ fraction (composed of 6% by weight of isobutene, 43% by weight of 1-butene, 25% by weight of 2-butene, 25% by weight of butanes and 1% by weight of others) obtained by removing butadiene and isobutene from a BB fraction obtained from a cracker of naphtha, was dehydrated by molecular sieve 13X. Then, 4 kg of the dehydrated $C_4$ fraction, 5.5 g of a n-hexane solution of nickel octanoate (Ni content: 6% by weight) and 11.3 g of ethylaluminum dichloride were charged under a nitrogen atmosphere to an induction agitation-type SUS autoclave having a capacity of 10 liters, and the mixture was reacted at 40° C. for 7 hours.

After the reaction, 340 g of a 5 wt % $H_2SO_4$ aqueous solution was added to the mixture to deactivate the catalyst, and then the mixture was subjected to liquid-liquid separation to obtain octenes.

The above reaction was repeated three times.

(2) Distillation to obtain an octene fraction

The octenes obtained in the above step (1) were rectified by Oldershow type distillation tower having an inner diameter of 50 mm and 20 plates under atmospheric pressure. An octene fraction having a tower top temperature of from 108° to 127° C. was obtained in an amount of 5.8 kg.

(3) Preparation of $C_9$ alcohol mixture (rhodium catalyst)

Into a SUS autoclave having a capacity of 10 liters, 2.0 kg of the octene fraction obtained in the above step (2) and 1.2 g of an aqueous rhodium acetate solution (10% as rhodium metal) were charged and reacted at a reaction temperature of 135° C. while maintaining the total pressure at a level of 160 kg/cm$^2$G by an oxo gas having a ratio of $H_2/CO=1$. Five hours later, the absorption of gas was no longer observed, and the reactor was cooled rapidly. The oxo gas was released, and the entire amount of the reaction solution was taken out and then subjected to distillation under reduced pressure of 10 mmHg to obtain aldehydes and alcohols. The total amount of the aldehydes and alcohols obtained was 99.2%.

Then, into a SUS autoclave having a capacity of 10 liters, the entire amount of the product obtained by the above distillation and 160 g of a nickel-supported solid catalyst were charged under a nitrogen atmosphere and reacted at a reaction temperature of 150° C. while maintaining the total pressure at a level of 90 kg/cm$^2$G with hydrogen gas.

Five hours later, the absorption of gas completed, and the reactor was cooled rapidly. The hydrogen gas was released, and the entire amount of the reaction solution was taken out. The solid catalyst was removed by filtration, and the filtrate was rectified by Oldershow type distillation tower having an inner diameter of 35 mm and 20 plates. The reflux ratio was 10, and the pressure was 10 mmHg. By this rectification, five types of $C_9$ alcohol mixtures (R-1, R-2, R-3, R-4 and R-5) were obtained. These five types of $C_9$ alcohol mixtures were analyzed by gas chromatography under the above-mentioned analytical conditions (1) to (7). The compositions of the $C_9$ alcohol mixtures are shown in Table 1.

(4) Evaluation of the properties of the plasticizer

The five types of $C_9$ alcohol mixtures (R-1, R-2, R-3, R-4 and R-5) obtained in the above step (3) were reacted with phthalic anhydride by a usual method for esterification, and then purified by a usual method to obtain a phthalate (plasticizer).

Polyvinyl chloride (polymerization degree n=1300): 100 PHR (parts per hundred parts of rubber or resin)

Plasticizer: 50 PHR

Stabilizer (cadmium-barium stearate): 1 PHR

Then, a mixture having the above composition was subjected to rolling by a usual method and then pressed to obtain a sheet having a thickness of 1 mm. Then, test pieces were punched out from the sheet by a dumbbel die. Each test piece was examined for the plasticizer properties. The results are shown in Table 2.

EXAMPLE 2

The operation was conducted in the same manner as in EXAMPLE 1 except that the hydroformylation reaction was conducted by using a cobalt catalyst.

Namely, into a SUS autoclave having a capacity of 10 liters, 2.0 kg of the octene fraction obtained in step (2) of EXAMPLE 1 and 20 g of dicobalt octacarbonyl were charged under a nitrogen atmosphere and reacted at a temperature of from 140° to 150° C. while maintaining the total pressure at a level of 160 kg/cm$^2$G with an oxo gas having a ratio of $H_2/CO=1$ Two hours later, the absorption of gas ceased, and the reactor was rapidly cooled. A 3% NaOH aqueous solution was injected to deactivate the cobalt catalyst. Then, the reactor was further cooled, and the oxo gas was released. Then, the entire amount of the reaction solution was taken out and subjected to liquid-liquid separation to obtain an organic phase.

Then, the organic layer was subjected to distillation under reduced pressure of 10 mmHg to obtain aldehydes and alcohols. The total amount of the aldehydes and alcohols obtained was 99%.

Then, into a SUS autoclave having a capacity of 10 liters, the entire amount of the product obtained by the above distillation and 160 g of a nickel-supported solid catalyst were charged under a nitrogen atmosphere and reacted at a reaction temperature of 150° C. while maintaining the total pressure at a level of 90 kg/cm$^2$G with hydrogen gas. Five hours later, the absorption of gas ceased, and the reactor was rapidly cooled. The hydrogen gas was released, and the entire amount of the reaction solution was taken out. The solid catalyst was removed by filtration, and the filtrate was rectified by Oldershow type distillation tower having an inner diameter of 35 mm and 20 plates. The reflux ratio was 10, and the pressure was 10 mmHg. By this rectification, five types of $C_9$ alcohol mixtures (C-1, C-2, C-3, C-4 and C-5) were obtained. These five types of $C_9$ alcohol mixtures were analyzed by gas chromatography under the same analytical conditions as in EXAMPLE 1. The compositions of the $C_9$ alcohol mixtures are shown in Table 1.

The $C_9$ alcohol mixtures were evaluated for the plasticizer properties in the same manner as in EXAMPLE 1(4). The results are shown in Table 2.

COMPARATIVE EXAMPLE 1

In the same manner as in EXAMPLE 1, a $C_9$ alcohol mixture was prepared, and by the rectification, four types of $C_9$ alcohol mixtures (HR-1, HR-2, HR-3 and HR-4) were obtained. Their compositions are shown in Table 1.

These $C_9$ alcohol mixtures were esterified in the same manner as in EXAMPLE 1 and then mixed with a vinyl chloride resin to examine the plasticizer properties. The results are shown in Table 2.

COMPARATIVE EXAMPLE 2

In the same manner as in EXAMPLE 2, a $C_9$ alcohol mixture was prepared, and by the rectification, four types of $C_9$ alcohol mixtures (HC-1, HC-2, HC-3 and HC-4) were obtained. Their compositions are shown in Table 1.

These $C_9$ alcohol mixtures were esterified and their plasticizer properties were examined in the same manner as in EXAMPLE 1. The results are shown in Table 2.

COMPARATIVE EXAMPLE 3

Bis(2-ethylhexyl)phthalate (DOP) was mixed with a vinyl chloride resin and its plasticizer properties were examined in the same manner as in EXAMPLE 1. The results are shown in Table 2.

TABLE 1

|  | EXAMPLE 1 | | | | | EXAMPLE 2 | | | | |
| --- | --- | --- | --- | --- | --- | --- | --- | --- | --- | --- |
|  | R-1 | R-2 | R-3 | R-4 | R-5 | C-1 | C-2 | C-3 | C-4 | C-5 |
| First group component (wt %) | 42.9 | 32.7 | 14.5 | 13.0 | 20.8 | 43.0 | 20.7 | 15.5 | 36.8 | 19.5 |
| Second group component (wt %) | 29.4 | 29.6 | 23.4 | 19.0 | 32.0 | 29.1 | 32.2 | 15.4 | 25.6 | 10.3 |
| Third group component (wt %) | 27.3 | 37.6 | 62.1 | 68.0 | 47.1 | 27.9 | 47.1 | 68.2 | 37.5 | 70.2 |

|  | COMPARATIVE EXAMPLE 1 | | | | COMPARATIVE EXAMPLE 2 | | | |
| --- | --- | --- | --- | --- | --- | --- | --- | --- |
|  | HR-1 | HR-2 | HR-3 | HR-4 | HC-1 | HC-2 | HC-3 | HC-4 |
| First group component (wt %) | 75.0 | 11.0 | 15.1 | 5.2 | 75.2 | 11.4 | 15.4 | 5.5 |
| Second group component (wt %) | 5.0 | 5.2 | 70.5 | 4.7 | 4.9 | 5.7 | 69.5 | 4.5 |
| Third group component (wt %) | 19.8 | 83.7 | 14.4 | 90.0 | 19.9 | 82.9 | 15.1 | 90.0 |

TABLE 2

|  | EXAMPLE 1 | | | | | EXAMPLE 2 | | | | |
| --- | --- | --- | --- | --- | --- | --- | --- | --- | --- | --- |
|  | R-1 | R-2 | R-3 | R-4 | R-5 | C-1 | C-2 | C-3 | C-4 | C-5 |
| Tensile force (kg/cm$^2$) | 276 | 275 | 290 | 277 | 280 | 282 | 270 | 277 | 276 | 275 |
| Elongation (%) | 361 | 358 | 330 | 328 | 340 | 352 | 345 | 331 | 349 | 351 |
| 100% modulus (kg/cm$^2$) | 125 | 126 | 128 | 127 | 127 | 124 | 126 | 129 | 127 | 126 |
| Evaporation (87° C. for 1 day) (%) | 1.59 | 1.5 | 1.0 | 0.98 | 1.2 | 1.54 | 1.35 | 1.09 | 1.40 | 1.00 |
| Cold resistance (Tf) (°C.) | −23.5 | −25.1 | −28.0 | −28.8 | −27.1 | −23.6 | −27.0 | −27.7 | −24.5 | −27.2 |
| Insulating properties (Volume resistance) (× 10$^{13}$ Ω · cm) | 28.0 | 22.1 | 12.5 | 10.5 | 14.0 | 29.5 | 31.0 | 10.8 | 25.5 | 14.1 |

|  | COMPARATIVE EXAMPLE 1 | | | | COMPARATIVE EXAMPLE 2 | | | | COMPARATIVE EXAMPLE 3 |
| --- | --- | --- | --- | --- | --- | --- | --- | --- | --- |
|  | HR-1 | HR-2 | HR-3 | HR-4 | HC-1 | HC-2 | HC-3 | HC-4 | DOP |
| Tensile force (kg/cm$^2$) | 272 | 274 | 280 | 269 | 269 | 280 | 275 | 277 | 269 |
| Elongation (%) | 370 | 320 | 330 | 328 | 368 | 325 | 331 | 330 | 320 |
| 100% modulus (kg/cm$^2$) | 123 | 128 | 129 | 130 | 124 | 127 | 128 | 130 | 123 |
| Evaporation (87° C. for 1 day) (%) | 1.80 | 0.97 | 1.20 | 0.88 | 1.75 | 0.99 | 1.18 | 0.87 | 3.0 |
| Cold resistance (Tf) (°C.) | −18.8 | −27.3 | −20.0 | −29.5 | −18.0 | −27.2 | −21.5 | −29.0 | −23.0 |
| Insulating properties (Volume resistance) (× 10$^{13}$ Ω · cm) | 36.8 | 8.2 | 9.8 | 4.1 | 37.1 | 8.0 | 9.2 | 3.9 | 10.0 |

As is evident from the EXAMPLES, the alcohol mixtures for plasticizer of the present invention are superior to conventional alcohols for plasticizer such as 2-ethylhexanol in the cold resistance and electrical insulating properties as the alcohol material for plasticizer for e.g. a vinyl chloride polymer. The present invention provides alcohol mixtures for plasticizer which are very useful from the industrial point of view.

We claim:

1. A method of preparing a $C_9$ alcohol mixture, comprising the steps of:

(a) obtaining a $C_9$ alcohol mixture by dimerizing butene fractions to obtain a $C_8$ olefin, hydroformylating the $C_8$ olefin and hydrogenating the hydroformylated product, and (b) distilling said alcohol mixture to obtain a distilled alcohol mixture comprising from 10–50% by weight of a first group component having a retention time not longer than the retention time of isobutyl n-caprylate, from 10–40% by weight of a second group component having a retention time longer than that of isobutyl n-caprylate and not longer than that of methyl n-caprate and from 30–70% by weight of a third group component having a retention time longer than that of methyl n-caprate, as divided into such three components by gas chromatography using a capillary column packed with a polyethylene glycol having a number average molecular weight of 15,000–20,000 as an isomer separating agent.

2. A process for preparing a plasticizer, comprising the steps of:

(a) obtaining a $C_9$ alcohol mixture by dimerizing butene fractions to obtain a $C_8$ olefin, hydroformylating the $C_8$ olefin and hydrogenating the hydroformylated product, and (b) distilling said alcohol mixture to obtain a distilled alcohol mixture comprising from 10–50% by weight of a first group component having a retention time not longer than the retention time of isobutyl n-caprylate, from 10–40% by weight of a second group component having a retention time longer than that of isobutyl n-caprylate and not longer than that of methyl n-caprate and from 30–70% by weight of a third group component having a retention time longer than that of methyl n-caprate, as divided into such three components by gas chromatography using a capillary column packed with a polyethylene glycol having a number average molecular weight of 15,000–20,000 as an isomer separating agent, and (c) reacting said distilled alcohol mixture with a carboxylic acid anhydride to form said plasticizer.

3. The method according to claim 1, wherein the distilled alcohol mixture comprises from 10 to 35% by weight of the first group component, from 10 to 40% by weight of the second group component and from 30 to 70% by weight of the third group component.

4. The method according to claim 1, wherein the distilled alcohol mixture comprises from 15 to 35% by weight of the first group component, from 10 to 40% by weight of the second group component and from 30 to 65% by weight of the third group component.

5. The method according to claim 1, wherein the distilled alcohol mixture comprises from 20 to 35% by weight of the first group component, from 10 to 40% by weight of the second group component and from 30 to 60% by weight of the third group component.

6. The method according to claim 1, wherein the distilled alcohol mixture comprises from 20 to 30% by weight of the first group component, from 15 to 33% by weight of the second group component and from 35 to 60% by weight of the third group component.

7. The method according to claim 2, wherein the distilled alcohol mixture comprises from 10 to 35% by weight of the first group component, from 10 to 40% by weight of the second group component and from 30 to 70% by weight of the third group component.

8. The method according to claim 2, wherein the distilled alcohol mixture comprises from 15 to 35% by weight of the first group component, from 10 to 40% by weight of the second group component and from 30 to 65% by weight of the third group component.

9. The method according to claim 2, wherein the distilled alcohol mixture comprises from 20 to 35% by weight of the first group component, from 10 to 40% by weight of the second group component and from 30 to 60% by weight of the third group component.

10. The method according to claim 2, wherein the distilled alcohol mixture comprises from 20 to 30% by weight of the first group component, from 15 to 33% by weight of the second group component and from 35 to 60% by weight of the third group component.

11. The method according to claim 1, wherein the hydroformylation is conducted using a rhodium catalyst.

12. The method according to claim 1, wherein the hydroformylation is conducted at a rhodium concentration of from 0.1 to 1,000 ppm as rhodium atom at a temperature from 80° to 200° C. under a pressure from atmospheric pressure to 500 kg/cm$^2$ and a H$_2$/CO volume ratio from 0.5 to 4.

13. The method according to claim 2, wherein the hydroformylation is conducted by means of a rhodium catalyst.

14. The method according to claim 2, wherein the hydroformylation is conducted at a rhodium concentration of from 0.1 to 1,000 ppm as rhodium atom at a temperature from 80° to 200° C. under a pressure from atmospheric pressure to 500 kg/cm$^2$G and a H$_2$/CO volume ratio from 0.5 to 4.

\* \* \* \* \*